United States Patent [19]
Zoeller et al.

[11] Patent Number: 6,159,896
[45] Date of Patent: Dec. 12, 2000

[54] IRIDIUM CATALYST FOR CARBONYLATION OF LOWER ALIPHATIC ALCOHOLS

[75] Inventors: Joseph Robert Zoeller; Andy Hugh Singleton; Gerald Charles Tustin, all of Kingsport; Donald Lee Carver, Church Hill, all of Tenn.

[73] Assignee: Eastman Chemical Company, Kingsport, Tenn.

[21] Appl. No.: 09/250,665

[22] Filed: Feb. 16, 1999

[51] Int. Cl.$^7$ .............................. B01J 29/06; B01J 21/18; B01J 23/40; B01J 23/74; B01J 27/13

[52] U.S. Cl. .............................. 502/326; 502/65; 502/66; 502/182; 502/185; 502/230; 502/302; 502/303

[58] Field of Search .................................. 502/326, 302, 502/230, 185, 182, 65, 66, 303

[56] References Cited

U.S. PATENT DOCUMENTS

| | | |
|---|---|---|
| 3,689,533 | 9/1972 | Schultz . |
| 3,717,670 | 2/1973 | Schultz . |
| 3,772,380 | 11/1973 | Paulik et al. . |
| 3,855,307 | 12/1974 | Rony et al. .............................. 260/604 |
| 3,856,856 | 12/1974 | Nozaki .................................... 260/532 |
| 3,897,328 | 7/1975 | Mitchell, III .......................... 502/223 |
| 3,969,221 | 7/1976 | Mitchell, III et al. ................. 502/223 |
| 4,024,052 | 5/1977 | Antos ...................................... 502/230 |
| 4,417,077 | 11/1983 | Drago et al. . |
| 4,612,387 | 9/1986 | Feitler . |
| 4,693,882 | 9/1987 | Setzer et al. . |
| 4,776,987 | 10/1988 | Luft et al. . |
| 4,781,868 | 11/1988 | Langerbeins ........................... 260/549 |
| 4,831,191 | 5/1989 | Larkin ..................................... 562/517 |
| 4,845,163 | 7/1989 | Panster et al. . |
| 4,918,218 | 4/1990 | Mueller et al. . |
| 5,144,068 | 9/1992 | Smith et al. . |
| 5,185,462 | 2/1993 | Evans et al. . |
| 5,218,140 | 6/1993 | Wegman . |
| 5,258,549 | 11/1993 | Pimblett . |
| 5,278,122 | 1/1994 | Correia et al. .......................... 502/185 |
| 5,488,143 | 1/1996 | Uhm et al. . |
| 5,510,524 | 4/1996 | Garland et al. . |
| 5,821,190 | 10/1998 | Kurabayashi et al. . |
| 5,900,505 | 5/1999 | Tustin et al. . |

FOREIGN PATENT DOCUMENTS

| | | |
|---|---|---|
| 0 120 631 A1 | 10/1984 | European Pat. Off. . |
| 0 130 058 A1 | 1/1985 | European Pat. Off. . |
| 0 461 802 A2 | 12/1991 | European Pat. Off. . |
| 0 596 632 A1 | 5/1994 | European Pat. Off. . |
| 0 752 406 A1 | 1/1997 | European Pat. Off. . |
| 0 759 419 A1 | 2/1997 | European Pat. Off. . |
| 1 390 625 | 4/1975 | United Kingdom . |
| 2 327 420 | 1/1999 | United Kingdom . |
| WO 98/33590A1 | 8/1998 | WIPO . |

OTHER PUBLICATIONS

J. Yang, A. Haynes and P. Maitlis, "The carbonylation of methyl iodide and methanol to methyl acetate catalysed by palladium and platinum iodides", *Chemical Communications*, No. 2,(Jan. 21, 1999). p. 179–180, Cambridge, UK.

K. M. Webber, B. C. Gates and W. Drenth, "Design and Synthesis of a Solid Bifunctional Polymer Catalyst for Methanol Carbonylation", *Journal of Molecular Catalysis*, 3 (1997/78) p. 1–9, Netherlands. Month n/a.

A. Krzywicki and M. Marczewski, "Formation and Evolution of the Active Site for Methanol Carbonylation on Oxide Catalysts Containing $RhCl_3$", *Journal of Molecular Catalysis*, 6 (1979) p. 431–440, Netherlands. Feb. 1979.

K. Fujimoto, J. Mazaki, K. Omata and H. Tominaga, "Promotion Effect of Hydrogen on Vapor Phase Carbonylation of Methanol Over Nickel on Active Carbon Catalyst", *Chemistry Letters*, (1987) p. 895–898, Japan. Month N/A.

H. E. Maneck, D. Gutschick, I. Burkardt, B. Leucke, H. Miessner, and U. Wolf, "Heterogeneous Carbonylation of Methanol on Rhodium Introduced Into Faujasite–Type Zeolites", *Catalysis Today*, 3 (1988) p. 421–429, Netherlands. Month N/A.

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 8, No. 8, (1988) p. 1315–1320, Great Britain. MonthN/A.

H. Yagita, K. Omata, H. Tominaga and K. Fujimoto, "Vapor– phase Carbonylation of Methanol Over Lead on Acitve Carbon Catalyst", *Catalysis Letters*, 2 (1989) p. 145–148, Germany. Feb. 1989.

H. Yagita and K. Jujimoto*, "Redox Cycle of Metal–on–Active Carbon Catalyst in the Vapor Phase Carbonylation of Methanol", *Journal of Molecular Catalyst*, 69 (1991) p. 191–197, Netherlands. Jun. 1991.

S. Bischoff, K. Omata and H. Yagita, "Hydrogen Effects on Nickel–Catalyzed Vapor–Phase Methanol Carbonylation", *Journal of Catalysis*, 133 (1992) p. 370–382. Mar. 1991.

M. J. Howard, M. D. Jones, M. S. Roberts and S. A. Taylor, "$C_1$ to Acetyls: Catalysis and Process", *Catalysis Today*, 18 (1993) p. 325–354, Amsterdam. Month N/A.

T. Liu and S. Chiu, "Promoting Effect of Tin on Ni/C Catalyst for Methanol Carbonylation", *Ind. Eng. Chem. Res.*, 33 (1994) p. 488–492, USA. Dec. 1993.

*Primary Examiner*—Mark L. Bell
*Assistant Examiner*—Patricia L. Hailey
*Attorney, Agent, or Firm*—Matthew W. Smith; Harry J. Gwinnell

[57] ABSTRACT

A catalyst comprising an effective amount of iridium and at least one second metal selected from the Lanthanide Series of the Periodic Table is useful for vapor phase carbonylation to produce carboxylic acids and esters from lower alkyl alcohols, ethers and ester-alcohol mixtures. The iridium and secondary metal are deposited on a support material, preferably carbon. In a preferred aspect of the invention, the catalyst is useful for vapor phase carbonylation to produce acetic acid, methyl acetate and mixtures thereof.

18 Claims, No Drawings

IRIDIUM CATALYST FOR CARBONYLATION OF LOWER ALIPHATIC ALCOHOLS

FIELD OF THE INVENTION

The present invention relates to a solid phase catalyst and more particularly to a catalyst for the vapor phase carbonylation of alkyl alcohols, ethers and ester-alcohol mixtures to produce esters and carboxylic acids. More particularly, the present invention relates to a supported catalyst which includes an effective amount of iridium and at least one second metal selected from the Lanthanide Series of the Periodic Table. The catalyst is particularly useful in the carbonylation of methanol to produce acetic acid, methyl acetate and mixtures thereof.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters, as illustrated in equations 1–3 below:

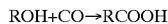
ROH+CO→RCOOH    (1)

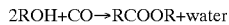
2ROH+CO→RCOOR+water    (2)

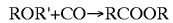
ROR'+CO→RCOOR    (3)

Carbonylation of methanol is a well known reaction and is typically carried out in the liquid phase with a catalyst. A thorough review of these commercial processes and other approaches to accomplishing the formation of acetyl from a single carbon source is described by Howard et al. in *Catalysis Today*, 18 (1993) 325–254. Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst.

U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions.

U.S. Pat. No. 5,510,524 teaches that the addition of rhenium improves the rate and stability of both the Ir-I and Rh-I homogeneous catalyst systems.

European Patent Application EP 0 752 406 A1 teaches that ruthenium, osmium, rhenium, zinc, cadmium, mercury, gallium, indium, or tungsten improve the rate and stability of the liquid phase Ir-I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle, and even higher rates.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772,380, describe the use of iridium on an inert support as a catalyst in the vapor phase, halogen-promoted, heterogeneous alcohol carbonylation process. European Patent Applications EP 0 120 631 A1 and EP 0 461 802 A2 describe the use of special carbons as supports for single transition metal component carbonylation catalysts.

European Patent Application EP 0 759 419 A1 pertains to a process for the carbonylation of an alcohol and/or a reactive derivative thereof.

EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium, and nickel, and an optional metal promoter on a carbon support. The optional metal promoter may be iron, nickel, lithium and cobalt. The conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3 (1988), 421–429. Gelin et al., in *Pure & Appl. Chem.*, Vol 60, No. 8, (1988) 1315–1320, provide examples of the use of rhodium or iridium contained in zeolite as catalysts for the vapor phase carbonylation of methanol in the presence of halide promoter. Krzywicki et al., in *Journal of Molecular Catalysis*, 6 (1979) 431–440, describe the use of silica, alumina, silica-alumina and titanium dioxide as supports for rhodium in the halide-promoted vapor phrase carbonylation of methanol, but these supports are generally not as efficient as carbon. Luft el al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Nickel on activated carbon has been studied as a heterogenecus catalyst for the halide-promoted vapor phase carbonylation of methanol, and increased rates are observed when hydrogen is added to the feed mixture. Relevant references to the nickel-on-carbon catalyst systems are provided by Fujimoto et al. In *Chemistry Letters* (1987) 895–898 and in *Journal of Catalysis*, 133 (1992) 370–382 and in the references contained therein. Liu et al., in *Ind. Eng. Chem. Res.*, 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general, the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2 (1989) 145–148 to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

A number of solid materials have been reported to catalyze the carbonylation of methanol without the addition of the halide promoter. Gates et al., in *Journal of Molecular Catalysis*, 3 (1977/78) 1–9, describe a catalyst containing rhodium attached to polymer bound polychlorinated thiophenol for the liquid phase carbonylation of methanol. Current, in European Patent Application EP 0 130 058 A1, describes the use of sulfided nickel containing optional molybdenum as a heterogeneous catalyst for the conversion of ethers, hydrogen and carbon monoxide into homologous esters and alcohols.

Smith et al., in European Patent Application EP 0 596 632 A1, describe the use of mordenite zeolite containing Cu, Ni, Ir, Rh, or Co as catalysts for the halide-free carbonylaticn of alcohols. Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140, describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometallalte anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase.

Certain disadvantages present in the prior art include instability of the carbonylation catalysts, lack of product selectivity, and in processes where there is a liquid phase present, the need for large and costly recovery equipment and procedures necessary for separation of products from the catalyst solutions, for catalyst recovery and catalyst recycle to reaction zone. Moreover, there are always handling losses of the catalyst.

Accordingly, there is a need for a catalyst which can be used in a vapor phase carbonylation process for the production of carboxylic acids and their esters and in which the, catalyst is maintained in the solid phase.

SUMMARY OF THE INVENTION

Briefly, the present invention relates to a solid supported catalyst for producing esters and carboxylic acids in a vapor phase carbonylation process and a process for making the catalyst composition. Suitable reactants for contacting the solid catalyst includes lower alkyl alcohols, ethers and ester-alcohol mixtures. The catalyst includes an effective amount of iridium and at least one second metal selected from metals having an atomic number of from 57 to 71, generally referred to as the Lanthanide Series of the Periodic Table. The iridium and at least one second metal are associated with a solid support material which, desirably, is inert to the carbonylation reaction.

It is an object of the invention to provide a catalyst composition having iridium and another metal selected from the Lanthanide Series of the Periodic Table associated with a solid support material.

It is another object of the invention to provide a solid phase catalyst composition for vapor phase carbonylation of methanol to form acetic acid or methyl acetate.

Another object of the invention is to provide a more selective and reactive carbonylation catalyst composition for the production of carboxylic acids.

Yet another object of the invention is to provide a catalyst composition which result in higher yields of acetic acid with minimum formation of ethers, aldehydes, and other undesirable by-products.

It is another object of the invention to provide a method for preparing the catalyst composition of the present invention.

These and other objects and advantages of the invention will become apparent to those skilled in the art from the accompanying detailed description.

DETAILED DESCRIPTON OF THE INVENTION

The catalyst of the present invention is particularly useful for the continuous production of carboxylic acids and esters by reacting lower alkyl alcohols, ethers and ester-alcohol mixtures in a vapor-phase carbonylation process. The catalyst includes an effective amount of iridium and at least one second metal selected from the group consisting of metals having an atomic number of from 57 to 71, generally referred to as the Lanthanide Series, associated with a solid support material. In a preferred embodiment, the catalyst is particularly useful in a vapor-phase carbonylation method for the continuous production of acetic acid, methyl acetate and mixtures thereof. Vapor-phase carbonylation is typically operated at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. In practice, this generally dictates a temperature range of about 100° C. to 500° C., with temperatures in the range of 100° C. to 325° C. being preferred and temperature of about 150° C. to 275° C. being particularly useful. Advantageously, operating in the vapor phase eliminates catalyst dissolution, i.e., metal leaching from the catalyst support, which occurs in the known heterogeneous processes operating in the presence of liquid compounds.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of about 0.1 to 100 bars absolute. The process preferably is carried out at a pressure in the range of about 1 to 50 bars absolute, most preferably, about 3 to 30 bar absolute.

Suitable feedstocks for carbonylation include lower alkyl alcohols, ethers, esters-alcohol mixtures and, as more fully discussed below esters, which may be carbonylated using the catalyst of the present invention. Non-limiting examples of feedstocks include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is the preferred feedstock to use with the solid supported catalyst of the present invention and is normally fed as methanol, it can be supplied in the form of a combination of materials which generate methanol. Examples of such materials include (i) methyl acetate and water and (ii) dimethyl ether and water. During carbonylation, both methyl acetate and dimethyl ether are formed within the reactor and, unless methyl acetate is the desired product, they are recycled with water to the reactor where they are converted to acetic acid. Accordingly, one skilled in the art will further recognize that it is possible to utilize the catalyst of the present invention produce a carboxylic acid from an ester feed material.

The presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the catalyst is used in a vapor-phase carbonylation process to produce methyl acetate, no water should be added and dimethyl ether becomes the preferred feedstock. Further, when methanol is used as the feedstock in the preparation of methyl acetate, it is necessary to remove water. However, the primary utility of the catalyst of the present invention is in the manufacture of acetic acid.

In practice, the lower alkyl alcohol, ester, and/or ether in the vapor phase is passed through or over the catalyst of the invention. The catalyst has an effective amount of iridium associated with a solid support material and at least one second metal selected from the group consisting of metals having an atomic number of from 57 to 71 of the Periodic Table. Desirably, the iridium and secondary metal are associated with the support material as a result of soluble impregnation of the iridium and the secondary metal which may result in either a salt of the iridium and/or metals, an oxide of the iridium and/or metals, or in a free metal being deposited on the support.

The solid support useful for acting as a carrier for the iridium and at least one secondary metal consists of a porous solid of such size that it can be employed in fixed or fluidized bed reactors. Typical support materials have a size of from about 400 mesh per inch to about ½ inch. Preferably, the support is carbon, including activated carbon, having a high surface area. Activated carbon is well known in the art and may be derived from coal or peat having a density of from about 0.03 grams/cubic centimeter (g/cm$^3$) to about 2.25 g/cm$^3$. The carbon can have a surface area of from about 200 square meters/grarr (m$^2$/g) to about 1200 m$^2$/g. Other solid support materials may be used, either alone or in combination, in accordance with the present invention include pumice, alumina, silica, silica-alumnina, magnesia, diatomaceous earth, bauxite, titania, zirconia, clays, magnesium silicate, silicon carbide, zeolites, and ceramics. The shape of the solid support is not particularly important and can be regular or irregular and include extrudates, rods, balls, broken pieces and the like disposed within the reactor.

The compound or form of iridium used to prepare the catalyst generally is not critical, and the catalyst may be prepared from any of a wide variety of iridium containing compounds. Indeed, iridium compounds containing myriad combinations of halide, trivalent nitrogen, organic compounds of trivalent phosphorous, carbon monoxide, hydrogen, and 2,4-pentane-dione, either alone or in combination. Such materials are available commercially and may be used in the preparation of the catalysts utilized in the present invention. In addition, the oxides of iridium may be used if dissolved in the appropriate medium. Preferably iridium is a salt of one of it chlorides, such as iridium trichloride or hydrated trichloride, hexacholoro-iridate and any of the various salts of hexachloroiridate(IV). One skilled in the art will understand that use of the preferred iridium complexes should be comparable on the basis of cost, solubility, and performance.

Similarly, the compound or form of the second metal compound used to prepare the catalyst generally is not critical, and the catalyst may be prepared using any of a wide variety of compounds containing the Lanthanide Series metals either alone or in combination. A wide variety of compounds of these elements containing various combinations of halides, acetates, nitrates, cyclopentadiene, and 2,4-pentane-dione, either alone or in combination, are available commercially and may be used in the preparation of the catalysts utilized in the process of the present invention. In addition, the oxides of these materials may be used if dissolved in the appropriate medium. Desirably, the compound used to provide the second metal is a water soluble form of the metal(s). Preferred sources include acetates, nitrates, and their halides. The most preferred source among these salts would be dictated by its solubility, preferably water solubility, which can vary widely across this list of useful second components. The most preferred secondary metals include lanthanum, cerium, praseodymium, and neodymium (Atomic numbers 57–60), or combinations thereof. The halides of such preferred secondary metals are generally commercially available and water soluble. Activity is still improved and costs are not necessarily prohibitive when the secondary metal is selected from samarium, europium, gadolinium, terbium, dysprosium, holmium, or erbium (atomic numbers 62–68) and mixtures of thereof.

The amount of iridium and secondary metal on the support can vary from about 0.01 weight percent to about 10 weight percent, with from about 0.1 weight percent to about 2 weight percent of each component being preferred.

The preparation of the solid support catalyst is carried out by preferably dissolving or dispersing the iridium and secondary metal component in a suitable solvent. The solid support material is then contacted and desirably impregnated with the iridium and secondary metal containing solutions. Various methods of contacting the support material with the iridium and secondary metal may be employed. For example, an iridium containing solution can be admixed with a secondary metal solution prior to impregnating the support material. Alternatively, the respective solutions can be impregnated separately into or associated with the support material prior to impregnating the support material with the second solution. For example, the secondary metal component may be deposited on a previously prepared catalyst support having the iridium component already incorporated thereon. Desirably, in this alternative embodiment, the support is dried prior to contacting the second solution. Similarly, the iridium and secondary metal (s) may be associated with the support material in a variety of forms. For example, slurries of the iridium and at least one secondary metal can be poured over the support material. Alternatively, the support material may be immersed in excess solutions of the active components with the excess being subsequently removed using techniques known to those skilled in the art. The solvent or liquid is evaporated, i.e. the solid support is dried so that at least a portion of the iridium and secondary metal is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

The solid supported catalyst may further be composed of two distinct components, namely the active catalyst metal component portion described above and a halogen promoting portion as the second component which can be catalytically active and which aids in the carbonylation process. The halogen promoter may be introduced at the catalyst preparation step or preferably, is introduced into the carbonylation reactor with the reactants. As a result of contacting the active metal components with the halogen promoter the ultimate active species of the iridium and secondary metal may exist as one or more coordination compounds or a halide thereof.

The liquid used to deliver the iridium and secondary metal in a form a solution, dispersion, or suspension is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobatanol, pentane, hexane, cyclohexane, heptane, toluene, pyridine, diethylamine, acetaldehyde, acetic acid, tetrahydrofuran and water.

In practice, a gaseous mixture having at least one of lower alkyl alcohol, ether and ester-alcohol mixture, either alone or in combination; carbon monoxide; and a halide are fed to a carbonylation reactor containing the iridium and secondary metal supported catalyst described above. The reactor is maintained under carbonylation conditions of Temperature and pressure. For example, if acetic acid is the desired product, the feedstock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone.

The carbon monoxide can be a purified carbon monoxide or include other gases. The carbon monoxide need not be of a high purity and may contain from about 1% by volume to about 99% by volume carbon monoxide, and preferably from about 70% by volume to about 99% by volume carbon monoxide. The remainder of the gas mixture including such gases as nitrogen, hydrogen, carbon dioxide, water and paraffinic hydrocarbons having from one to four carbon atoms. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The halide component of the feed includes one or more of chlorine, bromine and/or iodine and preferably, includes bromine and/or iodine which are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide ethyl iodide, 1-iodopropane, 2-iodobutane, 1-iodobutane, methyl bromide, ethyl bromide, and benzyl iodide. Desirably, the halide is a hydrogen halide or an alkyl halide having up to 6 carbon atoms. Non-limiting examples of preferred halides hydrogen iodide, methyl bromide and methyl iodide. The halide may also be a molecular halide such as $I_2$, $Br_2$, or $Cl_2$.

The amount of halide present to produce an effective carbonylation ranges from a molar ratio of about 1:1 to 10,000:1, with the preferred range being from about 5:1 to about 1000:1, wherein the molar ratio is based on methanol or methanol equivalents to halide.

In a preferred aspect of the invention, the vapor-phase carbonylation catalyst of the present invention may be used for making acetic acid, methyl acetate or a mixture thereof. The process includes the steps of contacting a gaseous mixture comprising methanol and carbon monoxide with the iridium/secondary metal catalyst described above in a carbonylation zone and recovering a gaseous product from the carbonylation zone.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner except as specified otherwise.

CATALYST 1

A catalyst in accordance with the present invention was prepared by dissolving 418 milligrams (mg) of iridium trichloride hydrate in 20 milliliters (ml) of distilled water to form a first solution. A second solution was prepared by dissolving 189 mg lanthanum oxide in 10 ml of concentrated hydrochloric acid. The first and second solutions were then combined and added to 20.0 grams (g) of 12×40 mesh activated carbon granules contained in an evaporating dish. The granules had a BET surface area in excess of 800 $m^2/g$. The mixture was heated using a steam bath and continuously stirred until it became free flowing. The mixture was then transferred to a 106 cm long×25 mm (outer diameter) quartz tube. The quartz tube was placed in a three-element electric tube furnace so that the mixture was located substantially in the center of the furnace heat zone. Nitrogen at a flow rate of 100 standard cubic centimeters per minute was continuously passed through the catalyst bed while the tube was heated from ambient temperature to 300° C. over a 2 hour period. The temperature was held at about 300° C. for 2 hours and then allowed to naturally cool back to ambient temperature. The catalyst prepared in this manner, designated as Catalyst 1, had 1.09 weight % iridium, 0.79 weight % lanthanum and a density of 0.57 g/ml.

COMPARATIVE CATALYSTS 1–3

The same procedure as above was repeated three times using the following catalysts:
1. catalyst CE-1 was prepared containing only iridium as the active metal;
2. catalyst CE-2 was prepared containing only lanthanum; and
3. catalyst CE-3 was prepared containing rhodium and lanthanum by substituting 282.3 mg (1.166 mmol) of rhodium trichloride trihydrate for the iridium trichloride hydrate.

CATALYST 2

A second catalyst in accordance with the present invention was prepared using the same procedure as above except that 537 mg (1.166 mmol) of cerium carbonate (III) hydrate was substituted for the lanthanum oxide. The catalyst, (Catalyst 2), had 1.07 weight % Ir, 0.78 weight % Ce and a density of 0.57 g per ml.

CATALYST 3

Examples 3–7 illustrate that a catalyst in accordance with the present invention can be prepared using a two step process. Accordingly, 414 mg (1.166 mmol) of praseodymium (III) chloride hexahydrate were dissolved in 30 mL of distilled water to form a first solution. The first solution was added to 20.0 g of 12×40 mesh activated carbon granules contained in an evaporating dish. The granules had a BET surface area in excess of 800 m2/g. The mixture was heated using a steam bath and continuously stirred until it became free flowing. The mixture was then transferred to a 106 cm long×25 mm (outer diameter) quartz tube. The quartz tube was placed in a three-element electric tube furnace so that the mixture was located in the approximate center of the 61 cm long heated zone of the furnace. Nitrogen at a flow rate of 100 standard cubic centimeters per minute was continuously passed through the catalyst bed while the tube was heated from ambient temperature to 300° C. over a 2 hour period. The temperature was held at 300° C. for 2 hours and then allowed to naturally cool back to ambient temperature.

A second solution was prepared by dissolving 412 mg of iridium trichloride hydrate in 30 mL of deionized water. The praseodymium impregnated activated carbon produced above was added to the second solution in an evaporating dish. The mixture was heated using a steam bath and occasionally stirred until it became free flowing. This mixture was then transferred to another 106 cm long×25 mm (outer diameter) quartz tube. The quartz tube was then placed in a three-element electric tube furnace so that the mixture was located approximately in the center of the 61 cm long furnace heating zone. Nitrogen, at a flow rate of 100 standard cubic centimeters per minute, was continuously passed through the catalyst bed while the tube was heated from ambient temperature to 300° C. over a 2 hour period. The temperature was held at 300° C. for 2 hours and then allowed to naturally cool back to ambient temperature.

The catalyst prepared in this manner designated as Catalyst 3. The catalyst had 1.08 weight % Ir, 0.79 weight % Pr, and a density of 0.57 g per ml.

CATALYST 4

The two step procedure described in Catalyst Example 3 above was repeated except that 418 mg (1.166 mmol) of neodymium (III) chloride hexahydrate was substituted for the praseodymium (III) chloride hexahydrate to obtain a catalyst (Catalyst 4). The catalyst had 1.08 weight percent Ir, 0.81 weight percent Nd and a density of 0.57 g per ml.

CATALYST 5

The two step procedure described in Catalyst Example 3 above was repeated except that 433 mg (1.166 mmol) of gadolinium (III) chloride hexahydrate was substituted for the praseodymium (III) chloride hexahydrate to obtain a catalyst (Catalyst 5). The catalyst had 1.07 weight percent Ir, 0.88 weight percent Gd and a density of 0.57 g per ml.

CATALYST 6

The two step procedure described in Catalyst Example 3 above was repeated except that 442 mg (1.166 mmol) of holmium (III) chloride hexahydrate was substituted for the praseodymium (III) chloride hexahydrate to obtain a catalyst (Catalyst 6). The catalyst had 1.07 weight percent Ir, 0.92 weight percent Ho and a density of 0.57 g per ml.

CATALYST 7

The two step procedure described in Catalyst Example 3 above was repeated except that 450 mg (1.166 mmol) of ytterbium (III) acetate hexahydrate was substituted for the praseodymium (III) chloride hexahydrate to obtain a catalyst (Catalyst 7). The catalyst had 1.07 weight percent Ir and 0.97 weight percent Yb and had a density of 0.57 g per mL.

CARBONYLATION OF METHANOL

In the examples which follow, the reactor consisted of a clean Hastelloy alloy tubing having dimensions of 800 to 950 mm (31.5 and 37 inch) long and an inside diameter of 6.35 mm (¼inch). The preheat and carbonylation reaction zones of the reactor were prepared by inserting into the tube a quartz wool pad approximately 410 mm from the top. The quartz wool pad occupied approximately 6 mm of the tubing length and acted as a support for the catalyst. Adjacent to the quartz wool pad the following materials were added: (1) a 0.7 g bed of fine quartz chips (840 microns); (2) 0.5 g of one of the above described catalysts; and (3) an additional 6 g of fine quartz chips which acted as a heat exchange surface to vaporize the liquid feeds. The top of the tube was attached to an inlet manifold for introducing liquid and gaseous feeds. The remaining lower length of tubing (product recovery section) acted as a condense. and consisted of a vortex cooler which varied in length depending on the original length of tubing employed and was maintained at approximately 0–5° C. during operation.

The gases were fed using Brooks flow controllers and liquids were fed using a high performance liquid chromatography pump. Care was taken not to allow any liquid feeds to contact the solid catalyst materials at any time, including assembly, start-up, and shutdown. The product reservoir tank was placed downstream from the reactor system. The pressure of the reactor was maintained using a Tescom 44-2300 pressure regulator on the outlet side of the reactor system and the temperature of the reaction section was maintained using heating tape on the outside of the tube.

Hydrogen and carbon monoxide were fed to the reactor when the reactor equilibrated at a temperature of about 240° C. and a pressure of 17.2 bara (250 psia). The hydrogen flow rate was maintained at 25 standard cubic centimeters per minute (cc/min). The carbon monoxide flow rate was maintained at 100 cc/min. The reactor was maintained under these conditions for 1 hour or until the temperature and pressure had stabilized, whichever was longer. The high pressure liquid chromatography pump was then started, feeding at a rate of 10–12 g per hour a mixture consisting of 70 weight percent methanol and 30 weight percent methyl iodide. Samples of the liquid product were collected and analyzed as indicated in Table 1 using gas chromatographic techniques known to those skilled in the art.

CARBONYLATION EXAMPLE 1

Samples of the product stream were taken as shown below during the methanol carbonylation for Catalyst I. The weight and composition of the each sample are set forth in Table 1. "Time" is the total time of operation of carbonylation as measured from the feeding of methanol until the indicated sample was taken. The values for methyl iodide ("MeI"), methyl acetate ("MeOAc"), methanol ("MeOH") and acetic acid ("HOAc") are weight percent based on the total weight of these compounds in the sample and was obtained using a flame ionization detector.

TABLE 1

| Sample Number | Time (hours) | MeI | MeOAc | MeOH | HOAc | Sample (grams) |
|---|---|---|---|---|---|---|
| 1 | 5 | 17.25 | 19.94 | 1.14 | 47.47 | 80.1 |
| 2 | 7 | 17.34 | 20.1 | 1.18 | 47.81 | 30.1 |
| 3 | 11 | 16.01 | 19 | 1.4 | 49.85 | 21.5 |
| 4 | 16.5 | 15.47 | 18.09 | 1.33 | 51.57 | 78.8 |
| 5 | 18.5 | 15.76 | 18.33 | 1.33 | 51.74 | 30.1 |
| 6 | 24 | 16.27 | 17.04 | 1.05 | 52.35 | 84.1 |
| 7 | 31 | 18.42 | 16.99 | 1.08 | 50.43 | 82.9 |
| 8 | 34 | 15.18 | 38.72 | 9.17 | 18.88 | 30.2 |
| 9 | 40 | 20.43 | 14.85 | 0.95 | 51.56 | 86.2 |
| 10 | 42 | 19.67 | 15.1 | 0.96 | 51.8 | 29.1 |
| 11 | 48 | 20.7 | 13.47 | 0.71 | 52.22 | 85.3 |
| 12 | 53 | 19.38 | 15.08 | 0.84 | 52.11 | 68.5 |
| 13 | 55 | 16.9 | 16.76 | 1.04 | 51.84 | 29.5 |
| 14 | 56.5 | 16.79 | 16.55 | 1.08 | 51.77 | 35.3 |
| 15 | 60 | 15.3 | 17.75 | 1.31 | 51.08 | 44.6 |
| 16 | 65 | 14.81 | 35.1 | 10.08 | 25.23 | 52.1 |

The rate of acetyl production based on the preceding experiment utilizing Catalyst I is Table 2 below. The Sample Number and Time values correspond to those of Table 1. "Acetyl Produced" represents the quantity, in millimoles, of methyl acetate and acetic acid produced during each increment of Time. Acetyl Produced is calculated from the formula:

$$\text{Acetyl Produced} = (\text{Sample weight (grams)}) \times 10 \times ((\text{weight \% of MeOAc}/74) + (\text{weight \% of AcOH}/60)).$$

"Production Rate" is the moles of Acetyl Produced per liter of catalyst volume per hour during each element of Time (Time Increment), i.e., the time of operation between samples. The formula for determining moles of Acetyl Produced per liter of catalyst volume per hour is determined as follows:

$$0.57 \times \text{Acetyl Produced}/(0.5 \times \text{Time Increment})$$

wherein 0.5 is the grams of catalyst used and 0.57 is the density of the catalyst in g/ml.

TABLE 2

| Sample Number | Acetyl Produced (mmol) | Rate (mol/L-h) |
|---|---|---|
| 1 | 849.6 | 193.7 |
| 2 | 321.6 | 183.3 |
| 3 | 233.8 | 66.6 |
| 4 | 869.9 | 180.3 |
| 5 | 334.1 | 190.4 |
| 6 | 927.4 | 192.2 |
| 7 | 887.1 | 144.5 |
| 8 | 253.0 | 96.2 |
| 9 | 913.7 | 173.6 |
| 10 | 310.6 | 177.0 |
| 11 | 897.7 | 170.6 |
| 12 | 734.5 | 167.5 |
| 13 | 321.7 | 183.4 |
| 14 | 383.5 | 291.5 |
| 15 | 486.7 | 158.5 |
| 16 | 466.2 | 106.3 |

Over the 60 hours of testing, the catalyst produced 9.19 moles of acetyl. This represents a rate of 283 moles of acetyl per kilogram of catalyst per hour (acetyl/$\text{kg}_{cat}$-h) or, represented as an hourly space velocity, 161 of acetyl/$\text{L}_{cat}$-h.

COMPARATIVE CARBONYLATION EXAMPLES 1–3 AND CARBONYLATION USING CATALYST 2–7

Catalysts 2–7 and comparative Example Catalysts CE-1-CE-3 were used in the corbonylation of methanol using the same procedure and parameters as described above. The Production Rate, expressed in terms of moles of Acetyl Produced per kilogram of catalyst per hour and moles per liter of catalyst volume per hour, for each of the catalysts is shown in Table 3 below.

TABLE 3

| Carbonylation | | Production Rate | |
|---|---|---|---|
| Example | Catalyst | moles/$kg_{cat}$-h | moles/$L_{cat}$-h |
| CE-1 | La | 2 | 1 |
| CE-2 | Ir | 93 | 53 |
| CE-3 | Rh—La | 242 | 138 |
| 2 | Ir—Ce | 195 | 111 |
| 3 | Ir—Pr | 159 | 90 |
| 4 | Ir—Nd | 238 | 135 |
| 5 | Ir—Gd | 213 | 121 |
| 6 | Ir—Ho | 280 | 159 |
| 7 | Ir—Yb | 85 | 49 |

As can be seen from Table 3, a carbonylation catalyst having iridium and at least one metal from the Lanthanide series produces exceptionally and quite unexpectedly, very high rates of acetyl production.

Although the present invention has been shown and described in terms of the presently preferred embodiment(s), it is to be understood that various modifications and substitutions, rearrangements of parts, components and process steps can be made by those skilled in the art without departing from the novel spirit and scope of the invention.

We claim:

1. A carbonylation catalyst useful for producing esters and carboxylic acids from reactants including lower alkyl alcohols, ethers, and ester-alcohol mixtures, said catalyst consisting essentially of from about 0.01 weight % to about 10 weight % of iridium and from about 0.01 weight % to about 10 weight % of at least one second metal selected from the group consisting of metals having an atomic number of from 57 to 7 1, wherein said iridium and at least one second metal have a valence greater than zero and are associated with a solid catalyst support material.

2. The carbonylation catalyst according to claim 1 wherein said solid support is carbon.

3. The carbonylation catalyst of claim 2 wherein said carbon support is activated carbon.

4. The carbonylation catalyst of claim 1 wherein said catalyst includes from about 0.1 weight percent to about 2 weight percent each of said iridium and said at least one second metal.

5. The carbonylation catalyst of claim 1 wherein said secondary metal is selected from the group consisting of lanthanum, cerium, praseodymium, neodymium, their respective salts, and mixtures thereof.

6. The carbonylation catalyst of claim 1 further comprising a second component comprising a halogen promoting component selected from the group consisting of molecular halides selected from the group consisting of $I_2$, $Br_2$, and $Cl_2$, hydrogen halides, gaseous hydriodic acid, alkyl and aryl halides having up to 12 carbon atoms, and mixtures thereof.

7. The carbonylation catalyst of claim 6 wherein said halogen promoting component is selected from the group consisting of hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof.

8. The carbonylation catalyst of claim 6 wherein said halogen promoting component is selected from the group consisting of hydrogen iodide, methyl iodide, hydrogen bromide, methyl bromide and mixtures thereof.

9. A catalyst useful for producing acetic acid, methyl acetate and mixtures thereof in a vapor-phase carbonylation process, said catalyst consisting essentially of from about 0.01 weight percent to about 10 weight percent of iridium and from about 0.01 weight % to about 10 weight % of at least one second metal selected from the group consisting of metals having an atomic number of from 57 to 7, wherein said iridium and said at least one second metal have a valence greater than zero and are associated with a solid catalyst support material selected from the group consisting of carbon, activated carbon, pumice, alumina, silica, silica-alumina, magnesia, diatomaceous earth, bauxite, titania, zirconia, clay, magnesaim silicate, silicon carbide, zeolites, ceramics and combinations thereof.

10. The carbonylation catalyst of claim 9 wherein said solid support is carbon.

11. The carbonylation catalyst of claim 9 wherein said solid support is activated carbon.

12. The carbonylation catalyst of claim 9 wherein said second metal is selected from the group consisting of lanthanum, cerium, praseodymium, neodymium, their respective salts, and mixtures thereof.

13. A carbonylation catalyst useful for producing acetic acid, methyl acetate and mixtures thereof in a vapor-phase carbonylation process, said catalyst consisting essentially of from about 0.01 weight percent to about 10 weight percent of iridium and from about 0.01 weight % to about 10 weight % of at least one second metal selected from the group consisting of lanthanum, cerium, praseodymium, neodymreium, their respective salts, and mixtures thereof, wherein said iridium and said at least one second metal have a valence greater than zero and are associated with a solid catalyst support material.

14. The carbonylation catalyst of claim 13 wherein said support is selected from the group consisting of carbon, activated carbon, pumice, alumina, silica, silica-alumina, magnesia, diatomaceous earth, bauxite, titania, zirconia, clay, magnesium silicate, silicon carbide, zeolites, ceramics and combinations thereof.

15. The carbonylation catalyst of claim 13 wherein said solid support is carbon.

16. The carbonylation catalyst of claim 13 wherein said solid support is activated carbon.

17. A method for preparing a solid supported catalyst composition useful for the vapor phase carbonylation of lower alkyl alcohols, ethers and ester-alcohol mixtures for producing esters and dicarboxylic acid, said method including the steps of:

a. providing a solid support material selected from the group consisting of carbon, activated carbon, pumice, alumina, silica, silica-alumina, magnesia, diatomaceous earth, bauxite, titania, zirconia, clays, magnesium silicate, silicon carbide, zeolites, ceramics and mixtures thereof;

b. contacting said support material with a solution containing iridium and at least one second metal selected from the group consisting of metals having an atomic number of from 57 to 71, and c. drying said solid support material wherein from about 0.01 weight percent to about 10 weight percent of said iridium and at least one second metal are associated with the solid catalyst support material and wherein said iridium and at least one second metal have a valency of greater than zero.

18. The method of claim 17 further comprising contacting said solid support material with a solution having at least one second component selected from the group consisting of $I_2$, $Br_2$, $Cl_2$, hydrogen iodide, methyl iodide, ethyl iodide, 1-iodopropane, 2-iodobutane, 1-iodobutane, methyl bromide, ethyl bromide, benzyl iodide and mixtures thereof.

* * * * *

UNITED STATES PATENT AND TRADEMARK OFFICE
CERTIFICATE OF CORRECTION

PATENT NO. : 6,159,896
DATED : December 12, 2000
INVENTOR(S) : Joseph Robert Zoeller; Andy Hugh Singleton, Gerald Charles Tustin and Donald Lee Carver It is certified that error appears in the above-identified patent and that said Letters Patent is hereby corrected as shown below:

Specification,
Column 6,
Line 40, after "meters" delete "grarr" and insert -- gram -- therefor.

Claim 9, column 14,
Line 5, after "57 to" delete "7," and insert -- 71, -- therefor.

Signed and Sealed this

Twenty-fifth Day of September, 2001

Attest:

NICHOLAS P. GODICI
*Attesting Officer* — *Acting Director of the United States Patent and Trademark Office*